United States Patent
Herken et al.

(10) Patent No.: US 10,206,581 B2
(45) Date of Patent: Feb. 19, 2019

(54) TRANSESOPHAGEAL OR TRANSTRACHEAL CARDIAC MONITORING BY OPTICAL SPECTROSCOPY

(71) Applicant: ZOLL Medical Corporation, Chelmsford, MA (US)

(72) Inventors: Ulrich Herken, Medford, MA (US); Annemarie Silver, Bedford, MA (US); Christopher L. Kaufman, Somerville, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 548 days.

(21) Appl. No.: 14/927,104

(22) Filed: Oct. 29, 2015

(65) Prior Publication Data

US 2016/0220117 A1  Aug. 4, 2016

Related U.S. Application Data

(60) Provisional application No. 62/072,096, filed on Oct. 29, 2014.

(51) Int. Cl.
| | | |
|---|---|---|
| A61B 5/00 | (2006.01) | |
| A61B 5/06 | (2006.01) | |
| A61B 5/02 | (2006.01) | |
| A61B 5/1459 | (2006.01) | |
| A61B 7/02 | (2006.01) | |

(Continued)

(52) U.S. Cl.
CPC .......... *A61B 5/0075* (2013.01); *A61B 5/0084* (2013.01); *A61B 5/02028* (2013.01); *A61B 5/061* (2013.01); *A61B 5/062* (2013.01); *A61B 5/065* (2013.01); *A61B 5/1459* (2013.01); *A61B 7/023* (2013.01); *A61B 5/0215* (2013.01); *A61B 5/0421* (2013.01); *A61B 2505/05* (2013.01)

(58) Field of Classification Search
CPC . A61B 5/4857; A61B 5/6898; A61B 10/0275; A61B 10/0291; A61B 17/42; A61B 1/00096; A61B 1/00177; A61N 2005/0628; A61N 2005/0652; A61N 5/0618
See application file for complete search history.

(56) References Cited

U.S. PATENT DOCUMENTS 3,695,253 A * 10/1972 Vielhauer ............ A61B 5/1135
600/508
4,331,156 A    5/1982 Apple et al.
(Continued)

FOREIGN PATENT DOCUMENTS

WO    WO 2014/011368 A1    1/2014

OTHER PUBLICATIONS

Adam Frisch et al., "Potential Utility of Near-Infrared Spectroscopy in Out-of-Hospital Cardiac Arrest: An Illustrative Case Series," Prehospital Emergency Care, Oct./Dec. 2012, vol. 16, No. 4, 2012.

(Continued)

*Primary Examiner* — Baisakhi Roy
(74) *Attorney, Agent, or Firm* — Robert D. Buyan; Stout, Uxa & Buyan, LLP (57) ABSTRACT

Devices, systems and methods useable for useable for monitoring a physiological variable in a target tissue or body fluid located within the thorax of a subject by optical spectroscopy.

42 Claims, 6 Drawing Sheets

(51) Int. Cl.
*A61B 5/0215* (2006.01)
*A61B 5/042* (2006.01)

(56) References Cited

U.S. PATENT DOCUMENTS

| | | | |
|---|---|---|---|
| 4,409,986 A | 10/1983 | Apple et al. | |
| 5,329,922 A | 7/1994 | Atlee | |
| 5,715,816 A | 2/1998 | Mainiero et al. | |
| 5,931,779 A | 8/1999 | Arakaki et al. | |
| 6,081,740 A * | 6/2000 | Gombrich | A61B 5/0071 |
| | | | 600/117 |
| 6,212,424 B1 | 4/2001 | Robinson | |
| 6,471,653 B1 | 10/2002 | Jordfald et al. | |
| 6,626,841 B1 | 9/2003 | Atlee | |
| 6,884,220 B2 | 4/2005 | Aviv et al. | |
| 6,990,364 B2 | 1/2006 | Ruchti et al. | |
| 7,245,373 B2 | 7/2007 | Soller et al. | |
| 7,299,079 B2 * | 11/2007 | Rebec | A61B 5/14532 |
| | | | 600/310 |
| 7,613,489 B2 | 11/2009 | Myers | |
| 7,647,092 B2 | 1/2010 | Motz et al. | |
| 7,850,610 B2 | 12/2010 | Ferek-Petric | |
| 8,172,758 B2 | 5/2012 | Harhen | |
| 8,277,385 B2 | 10/2012 | Berka et al. | |
| 8,346,329 B2 | 1/2013 | Xu et al. | |
| 8,406,838 B2 | 3/2013 | Kato | |
| 8,641,627 B2 | 2/2014 | Roth et al. | |
| 8,649,849 B2 | 2/2014 | Liu et al. | |
| 9,087,368 B2 * | 7/2015 | Tearney | A61B 5/0062 |
| 2004/0220478 A1 | 11/2004 | Wallace | A61B 1/00096 |
| | | | 600/476 |
| 2006/0106283 A1 * | 5/2006 | Wallace | A61B 1/00096 |
| | | | 600/109 |
| 2006/0106375 A1 | 5/2006 | Werneth et al. | |
| 2006/0194261 A1 * | 8/2006 | Kim | G01N 33/5008 |
| | | | 435/7.2 |
| 2006/0198128 A1 * | 9/2006 | Piepgras | B29C 39/10 |
| | | | 362/147 |
| 2007/0135803 A1 * | 6/2007 | Belson | A61B 1/00154 |
| | | | 606/1 |
| 2009/0318787 A1 | 12/2009 | Aoyagi et al. | |
| 2010/0106025 A1 * | 4/2010 | Sarfaty | A61B 5/0075 |
| | | | 600/476 |
| 2010/0198346 A1 * | 8/2010 | Keogh | A61F 2/2433 |
| | | | 623/2.11 |
| 2010/0262000 A1 * | 10/2010 | Wallace | A61B 1/00096 |
| | | | 600/424 |
| 2011/0184683 A1 | 7/2011 | Soller et al. | |
| 2013/0225955 A1 | 8/2013 | Schenkman et al. | |
| 2013/0231573 A1 | 9/2013 | Zeng et al. | |
| 2014/0005465 A1 * | 1/2014 | Ribbing | A61N 5/103 |
| | | | 600/3 |
| 2014/0024904 A1 | 1/2014 | Takinami | |
| 2014/0135647 A1 | 5/2014 | Wolf, II | |
| 2014/0190481 A1 * | 7/2014 | Jam | A61M 16/0006 |
| | | | 128/203.12 |
| 2015/0216398 A1 * | 8/2015 | Yang | A61B 1/043 |
| | | | 600/109 |
| 2016/0123802 A1 * | 5/2016 | Likovich | G01J 1/0271 |
| | | | 356/221 |
| 2017/0000353 A1 * | 1/2017 | Li | A61B 1/2733 |
| 2017/0181802 A1 * | 6/2017 | Sachs | A61B 34/35 |
| 2017/0224257 A1 * | 8/2017 | Rogers | A61B 5/1455 |
| 2017/0273671 A1 * | 9/2017 | Reich | A61B 10/0275 |

OTHER PUBLICATIONS

John R. Wilson et al., "Noninvasive Detection of Skeletal Muscle Underperfusion with Near-Infrared Spectroscopy in Patients with Heart Failure," Circulation, vol. 80, No. 6, Dec. 1989, pp. 1668-1674.
PCT International Search Report dated Feb. 4, 2016 in related PCT Application No. PCT/US2015/058089.
M. Mullner et al., "Near Infrared Spectroscopy During and After Cardiac Arrest—Preliminary Results," Clinical Intensive Care, vol. 6, No. 3, pp. 107-111 (1995). Abstract.
Bhunia, S. K. et al., "Implanted Near-Infrared Spectroscopy for Cardiac Monitoring", Proc. SPIE 7896, Optical Tomography and Spectroscopy of Tissue IX, 789632 (2011). [http://proceedings.spiedigitallibrary.org/proceeding.aspx?articleid=733147].

* cited by examiner

TRANSESOPHAGEAL OR TRANSTRACHEAL CARDIAC MONITORING BY OPTICAL SPECTROSCOPY

RELATED APPLICATION

This application claims priority to U.S. Provisional Patent Application No. 62/072,096 filed Oct. 29, 2014, the entire disclosure of which is expressly incorporated herein by reference.

FIELD OF THE INVENTION

The present invention relates to the fields biology, medicine and biomedical engineering and more particularly to devices, systems and methods useable for transesophageal or transtracheal cardiac monitoring by optical spectroscopy.

BACKGROUND OF THE INVENTION

Pursuant to 37 CFR 1.71(e), this patent document contains material which is subject to copyright protection and the owner of this patent document reserves all copyright rights whatsoever.

In the late 1980's NIRS was determined to be useable to noninvasively assess skeletal muscle oxygenation ($SmO_2$) in patients with heart failure by comparing light absorption at 760 nm and 800 nm as indicia of hemoglobin-myoglobin oxygenation. Wilson, J. R. et al.; *Noninvasive Detection Of Skeletal Muscle Underperfusion With Near-Infrared Spectroscopy In Patients With Heart Failure;* Circulation, 80(6), Pages 1668-74 (1989). Since then, NIRS has been studied for use in measuring oxygenation concentration as well as other physiological variables and analytes in various organs and tissues of the body. In contrast to typical pulse oximetry, which generally measures oxygen in the flowing blood, NIRS can be used to measure whether or not enough oxygen is being delivered to meet the metabolic demand of a particular organ or tissue (e.g., skeletal muscle, heart, brain, etc.).

NIRS has been studied for use in monitoring the oxygen content of certain body tissues during and following cardiopulmonary resuscitation (CPR). In one such study, regional cerebrovascular oxygen saturation ($rSO_2$) was monitored by placing an infrared light-emitting probe on the patient's forehead after arrival in the hospital emergency department. Patients who survived for one week had significantly higher median $rSO_2$ on arrival than nonsurvivors. Also, patients who arrived while undergoing CPR without spontaneous circulation had lower median $rSO_2$ than patients who arrived after restoration of spontaneous circulation (ROSC). Patients with ROSC who went on to survive for one week had a higher $rSO_2$ on arrival than patients with ROSC who did not survive for one week. These investigators concluded that low $rSO_2$ after cardiac arrest was associated with a higher mortality and that non-invasive monitoring of cerebrovascular oxygen saturation by NIRS could potentially be useful in prognosticating outcomes for patients following cardiac arrest. Mullner, M., et al., *Near Infrared Spectroscopy During And After Cardiac Arrest—Preliminary Results;* Clinical Intensive Care, Vol. 6, No. 3, Pages 107-11 (1995).

In a more recent study, patients who had experienced out-of hospital cardiac arrest followed by ROSC were monitored by an NIRS $StO_2$ monitor and by an end-tidal carbon dioxide ($ETCO_2$) monitor. $ETCO_2$ had previously been established and an indicator of ROSC or rearrest. Downward trends in $StO_2$ were observed prior to each rearrest and rapid increases in $StO_2$ were noted after ROSC. The $StO_2$ data showed less variance than the $ETCO_2$ data in the periarrest period. The investigators concluded that a decline in $StO_2$ level may correlate with rearrest and, thus, may be useful as a predictor of rearrest in post-cardiac arrest patients. A rapid increase in $StO_2$ was also seen upon ROSC and may be a better method of identifying ROSC during CPR than pauses for pulse checks or $ETCO_2$ monitoring. Frisch, A., et al.; *Potential Utility of Near-Infrared Spectroscopy in Out-of-Hospital Cardiac Arrest: An Illustrative Case Series;* Prehospital Emergency Care, Vol. 16, No. 4: Pages 564-570 (2012).

Additionally, investigators have explored the use of a subcutaneously implanted NIRS device in combination with an Implanted Cardioverter Defibrillator (ICD). In this study, NIRS oximetric measurements were used, in combination with electrical monitoring by the ICD, to distinguish between the onset of a ventricular arrhythmia requiring defibrillation and mere electromagnetic interference or artifacts resulting from erroneous double counting of the electrocardiographic T-wave as an R-wave, ICD lead failure, or other electrocardiographic aberrancies. Bhunia, S. K. et al., *Implanted Near-Infrared Spectroscopy For Cardiac Monitoring;* Proc. SPIE 7896, Optical Tomography and Spectroscopy of Tissue IX, 789632 (2011). [http://proceedings.spiedigitallibrary.org/proceeding.aspx?articleid=733147]

The prior art has included a number of NIRS devices that are positionable at various locations on the patients skin, or subcutaneously below the skin, to measure physiological properties or concentrations of analytes (e.g., pH, temperature, oxygen tension, oxygen saturation, partial pressure of oxygen, partial pressure of carbon dioxide, hemoglobin concentration, water concentration, hematocrit, glucose concentration, presence of biomarkers, etc.) in underlying organs or tissues. Some but not necessarily all examples of such devices are described in U.S. Pat. No. 5,931,779 (Arakaki, et al.); U.S. Pat. No. 6,212,424 (Robinson); U.S. Pat. No. 6,990,364 (Ruchti et al.); U.S. Pat. No. 7,245,373 (Soller, et al.); U.S. Pat. No. 7,613,489 (Myers); U.S. Pat. No. 7,647,092 (Motz et al.); U.S. Pat. No. 8,277,385 (Berka et al.); U.S. Pat. No. 8,346,329 (Xu et al.); U.S. Pat. No. 8,406,838 (Kato) and U.S. Pat. No. 8,649,849 (Liu et al.) as well as United States Patent Application Publication Nos. 2014/0135647 (Wolf II); 2014/0024904 (Takinami); 2013/0225955 (Schenkman, et al.) and 2011/0184683 (Soller et al.), the entire disclosure of each such patent and patent application being expressly incorporated herein by reference. Also, examples of such devices are currently marketed as CareGuide™ Oximeters (Reflectance Medical, Inc., Westborough, Mass.); INVOS™ Somatic/Cerebral Oximetry Monitors (Covidien Respiratory and Monitoring Solutions, Boulder, Colo.); Reveal LINQ™ Insertable Cardiac Monitoring Systems (Medtronic Corporation, Minneapolis, Minn.); FORE-SIGHT ELITE® Cerebral Oxygen Monitors (CAS Medical Systems, Inc., Branford, Conn.) and EQUANOX™ Cerebral/Somatic Tissue Oximetry Devices (Nonin Medical, Inc., Plymouth, Minn.). Some if not all of these NIRS devices utilize specialized apparatus and/or signal processing techniques (e.g., "background subtraction") to minimize or eliminate spectral effects from skin, bone or other intervening tissue that resides between the location of the NIRS device and the organ or tissue of interest.

In the past, certain devices have been positioned within the esophagus adjacent to the heart to monitor or image the heart from a vantage point that has minimal intervening tissue between the device and the heart. For example, endoesophageal stethoscopes and pulse monitoring probes have been advanced into the esophagus and used to monitor a patient's heartbeat, examples of which are described in U.S. Pat. No. 4,409,986 (Apple et al.); U.S. Pat. No. 4,331,156 (Apple, et al.). Also, ultrasound probes have been inserted into the esophagus and used for transesophageal echocardiography, examples of which are described in U.S. Pat. No. 8,641,627 (Roth et al.); U.S. Pat. No. 8,172,758 (Harhen); U.S. Pat. No. 6,884,220 (Aviv et al.) and U.S. Pat. No. 6,471,653 (Jordfald, et al.).

Additionally, United States Patent Application Publication No. 2013/0231573 (Zeng et al.) describes the insertion of a near-infrared spectroscopy probe through the working channel of a bronchoscope and the use of such probe to for endobroncheal Raman spectroscopic analysis of lung cancer tissue.

Given that NIRS and other forms of optical spectroscopy used for measuring the physiologic status of living tissue (broadly termed "Physiologic Spectroscopy" (PS)) are a potentially valuable tool for monitoring cardiac tissue or a subject's blood at specific locations in emergency and critical care situations, it is desirable to develop new optical spectroscopy monitoring devices and methods which are useable for obtaining optical spectrographic measurements from cardiac tissue or from blood located within the chambers of the heart or great vessels (e.g., pulmonary artery, aorta, etc.), and other tissues within the vicinity of the esophagus, the trachea or the main bronchi.

SUMMARY OF THE INVENTIONS

The present invention generally provides devices and methods wherein an optical spectroscopy device is inserted into an intrathoracic body lumen (e.g., the esophagus, trachea or a bronchus) and used for PS monitoring of cardiac tissue or blood located within the heart or great vessels (e.g., aorta, pulmonary artery, pulmonary vein, etc.).

In accordance with the present invention, there are provided systems for monitoring a physiological variable in a target tissue or body fluid located within the thorax of a subject by optical spectroscopy. Such systems may comprise an elongate body that is configured for insertion into the intrathoracic body lumen and an PS system located on that elongate body. Such PS system may comprise an i) an emitter (e.g., one or more LEDs) for emitting near infrared light through the wall of the body lumen into a target tissue or body fluid located in the heart, chamber of the heart or intrathoracic blood vessel and ii) a detector for detecting light that has been emitted from the emitter after said light has undergone dispersion and/or reflection by the target tissue or body fluid. Additionally, the system may include a processing device (e.g., a microprocessor, computer, etc.) programmed to use signals received from the detector to estimate at least one physiological variable within the target tissue or body fluid. In some embodiments, the system may also include a locator apparatus to assist in locating the intended target area and maneuvering the PS system into an operative position from which it may measure the intended physiological variable from the intended target location.

Further in accordance with the present invention, the target location from which the physiological variable is measured may be any intrathoracic tissue or body fluid, for example, an area of myocardial or other cardiac tissue or blood that is coursing through or is contained in a chamber of the heart or intrathoracic blood vessel (e.g., aorta, pulmonary artery, pulmonary vein, etc.).

Still further in accordance with the present invention, the physiological variable being measured from the target location may be, for example, temperature, oxygen tension, oxygen saturation, partial pressure of oxygen, partial pressure of carbon dioxide, hemoglobin concentration, water concentration, hematocrit, glucose concentration or the presence/absence of a biomarker.

Still further aspects and details of the present invention will be understood upon reading of the detailed description and examples set forth herebelow.

DETAILED DESCRIPTION OF THE INVENTION

The following detailed description and the accompanying drawings to which it refers are intended to describe some, but not necessarily all, examples or embodiments of the invention. The described embodiments are to be considered in all respects as illustrative and not restrictive. The contents of this detailed description and the accompanying drawings do not limit the scope of the invention in any way.

Figure 1A:
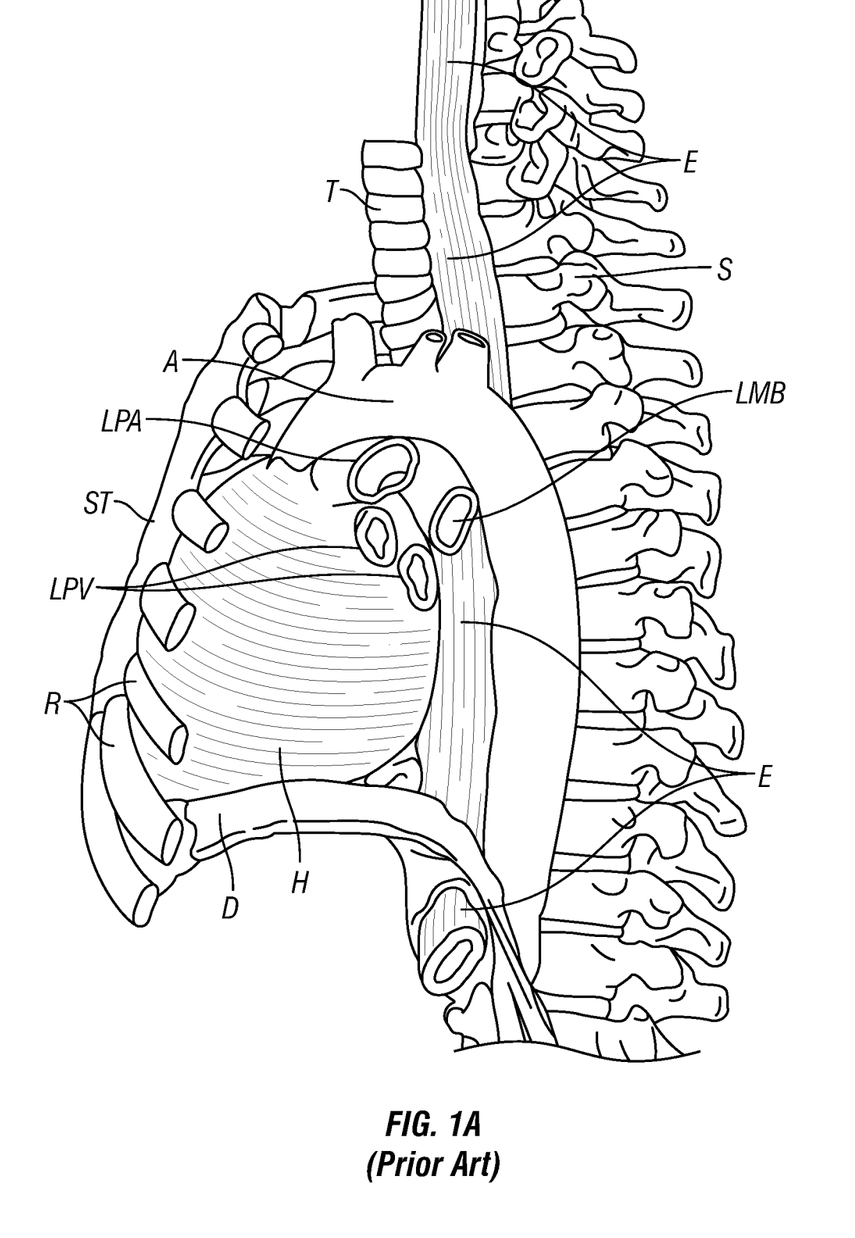
FIG. 1A is a diagram showing typical anatomy of a human heart with adjacent portions of the esophagus, tracheobroncheal tree and major blood vessels.
Figure 1B:
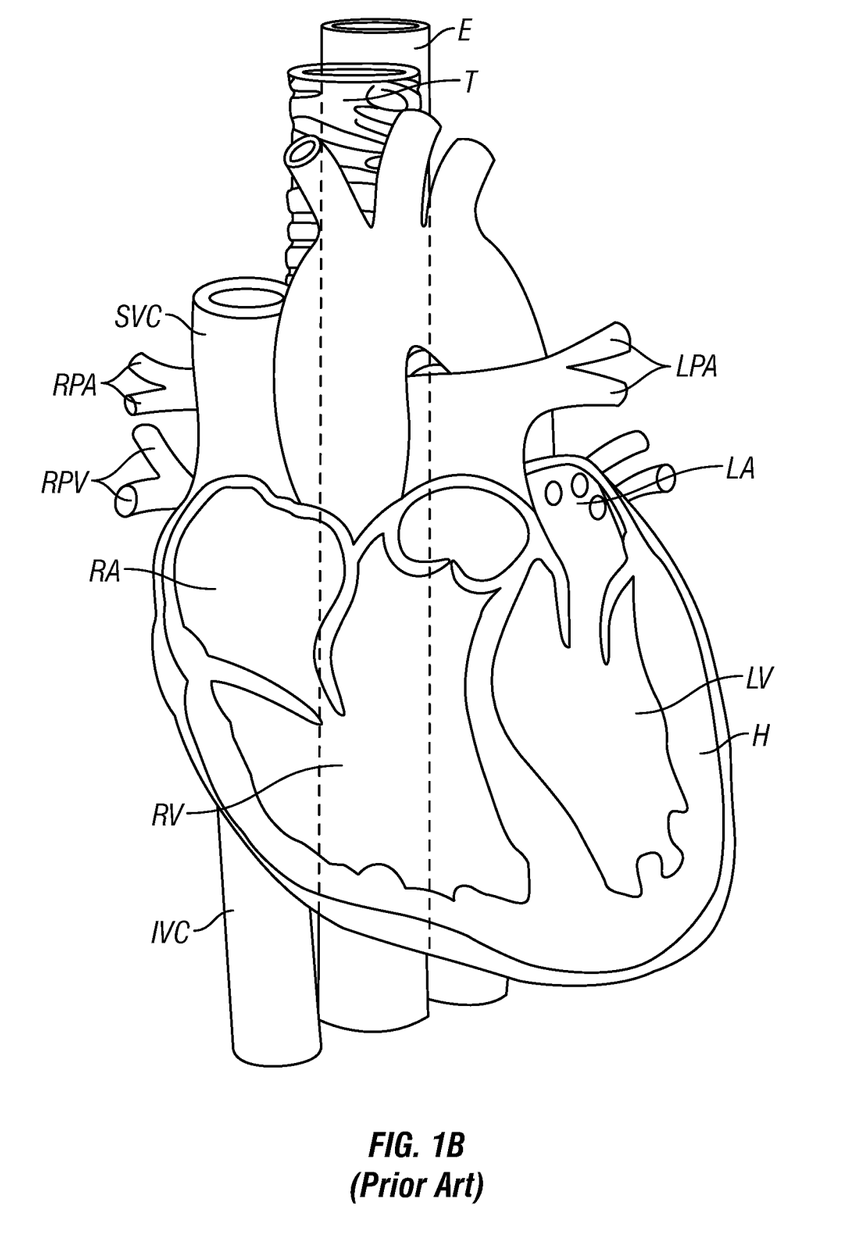
FIG. 1B is a diagram showing the anatomy of FIG. 1 wherein the hear is shown in a sagittal sectional view so as to reveal the locations of the cardiac chambers relative to the adjacent region of the esophagus.
Figures 2, 2A:
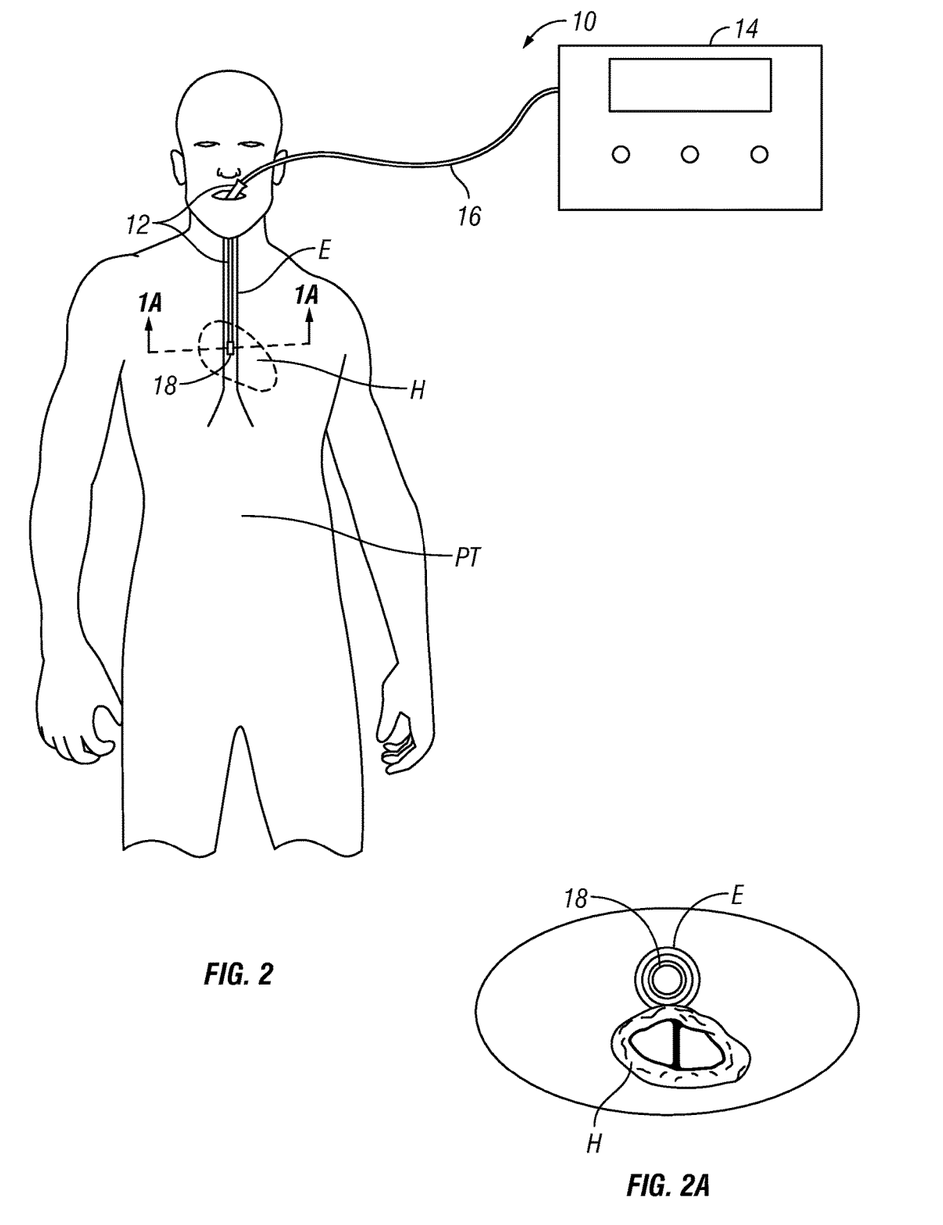
FIG. 2 is a schematic diagram showing an esophageal PS monitoring system of the present invention being used to perform PS cardiac monitoring of a human patient.
FIG. 2A is a schematic cross sectional diagram showing a transesophageal NIRS device positioned within the esophagus adjacent to the heart.
Figure 6:
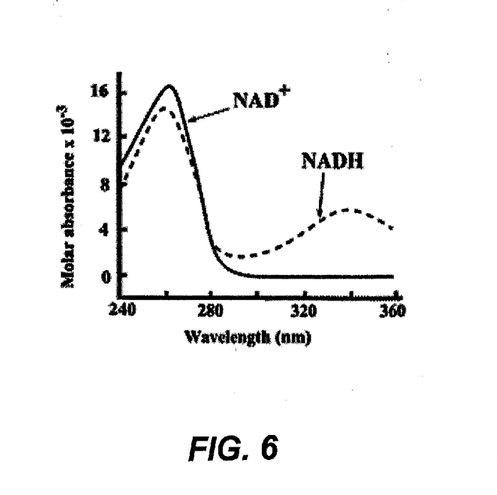
FIG. 6 is a graph (reproduced from Wikipedia (http://en.wikipedia.org/wiki/Nicotinamide_adenine_dinucleotide) showing relative changes in the concentrations of oxidized nicotinamide adenine dinucleotide (NAD) and its reduced form NADH.

FIGS. 1 and 2 show portions of the intrathoracic anatomy, with specific organs and anatomical structures being identified as follows:

A Aorta
H Heart
E Esophagus
D Diaphragm
T Trachea
S Spine
R Ribs
RA Right Atrium
RV Right Ventricle
LA Left Atrium
LV Left Ventricle
IVC Inferior Vena Cava
SVC Superior Vena Cava
LMB Left Main Bronchus
LPA Left Pulmonary Arteries
RPA Right Pulmonary Arteries
LPV Left Pulmonary Veins
RPV Right Pulmonary Veins Reference to some of all of these anatomical structures is made in the description of examples set forth below. The term "heart" is to be interpreted broadly to include the myocardium, infarcted myocardium (if present), chambers of the heart (e.g., blood located therewithin), AV/SA nodes, Purkinje fibers or other locations in the heart's electrical conduction system. In considering the examples described below, it should be appreciated that the devices and methods of the present invention are useable to obtain oximetric measurements from the central circulation or heart, while prior art devices that measure $StO_2$, $rSO_2$, etc. are limited to sensing sites that represent peripheral circulation or tissue microcirculation. The peripheral circulation as well as its signal from NIRS can be dramatically limited by peripheral vasopressors or vasodilators, as was described in Frisch, A., et al.; *Potential Utility of Near-Infrared Spectroscopy in Out-of-Hospital Cardiac Arrest: An Illustrative Case Series;* Prehospital Emergency Care, Vol. 16, No. 4: Pages 564-570 (2012). In that reported study, $StO_2$ readings obtained from subjects who had received large doses of epinephrine were less indicative of loss of spontaneous circulation or ROSC than in other subjects who had not received large doses of epinephrine. In this respect, the intrathoracic NIRS devices and methods of the present invention offer significant advantages over prior art NIRS devices which are positioned topically on the skin or subcutaneously under the skin bit still outside of the thoracic cavity. It has also been shown that the spectrographic information in the visual light and ultraviolet range are also physiologically relevant. For instance the metabolic status can be assessed by measuring the relative concentrations of oxidized nicotinamide adenine dinucleotide NAD and the reduced form NADH, as shown in the graph of FIG. 6.

Epidermal tissue tends to fluoresce in UV light so it is not possible to measure NADH/NAD from a surface probe. An esophageal approach to the sensing will allow for measurements of not only the esophageal wall but all the tissues in the region of the esophagus. Even NIRS systems will use light in the visible range e.g. 600-2500 nm), thus the NIRS systems are not strictly in the near-infrared range. We therefore use the broader terminology of Physiologic Spectroscopy (PS), or alternatively "optical spectroscopy" rather than just NIRS to describe the full range of wavelengths used for analyzing the physiologic status of living tissue to describe the invention.

FIG. 2 et seq. show some non-limiting examples of PS monitoring systems which are useable for intrathoracic monitoring in accordance with the present invention. In particular, FIG. 2 is a schematic showing of one type of monitoring system 10 of the present invention useable to perform transesophageal intrathoracic monitoring. This system 10 comprises an elongate apparatus 12 having an PS system 18, connecting cable(s) 16 and a processing/display apparatus 14. The elongate apparatus 12 has been inserted into the esophagus E or a patient PT and maneuvered to an operative position from which the PS system 18 will measure a desired variable from a target tissue or body fluid located within the patient's thoracic cavity. The target tissue or body fluid may be, for example, an area of myocardial or other cardiac tissue or blood that is flowing through, or is contained in, a chamber of the heart or intrathoracic blood vessel. The PS system 18 comprises one or more emitter(s) which emit(s) near infrared light and a detector for detecting the emitted light after it has undergone dispersion and/or reflection by the target tissue or body fluid. Signals received by the detector are transmitted through cable(s) 16 to the processing/display apparatus 14. The processing/display apparatus includes a microprocessor, computer or other processing device that is programmed to use signals received from the detector to estimate at least one physiological variable within the target tissue or body fluid. The physiological variable may, for example, be selected from: temperature, oxygen tension, oxygen saturation, partial pressure of oxygen, partial pressure of carbon dioxide, hemoglobin concentration, water concentration, hematocrit, glucose concentration and presence of a biomarker.

The PS system 18 and processor/display 14 may be constructed, programmed and function in any suitable way including, for example, in any of the ways described in U.S. Pat. No. 5,931,779 (Arakaki, et al.); U.S. Pat. No. 6,212,424 (Robinson); U.S. Pat. No. 6,990,364 (Ruchti et al.); U.S. Pat. No. 7,245,373 (Soller, et al.); U.S. Pat. No. 7,613,489 (Myers); U.S. Pat. No. 7,647,092 (Motz et al.); U.S. Pat. No. 8,277,385 (Berka et al.); U.S. Pat. No. 8,346,329 (Xu et al.); U.S. Pat. No. 8,406,838 (Kato) and U.S. Pat. No. 8,649,849 (Liu et al.) as well as United States Patent Application Publication Nos. 2014/0135647 (Wolf II); 2014/0024904 (Takinami); 2013/0225955 (Schenkman, et al.) and 2011/0184683 (Soller et al.), the entire disclosures of which are expressly incorporated herein by reference. More specifically, in at least some embodiments of the invention, the processing device may receive spectral information from the detector which it then compares to a set (e.g., a library) of stored reference spectra. Those reference spectra may have been predetermined from previously compiled clinical or experimental data or from data determined from a model of light attenuation in the selected target tissue or body fluid. The processor may then identify a member of the set of reference spectra that corresponds to the measured spectral information. The processor may then apply a set of correction factors to correct for intervening tissue(s) or other items that distort or interfere with the spectral information and then uses the corrected identified member of the set of spectra as input to a calibration equation to determine a value associated with the particular physiological variable being measured. However, because the present invention provides for positioning the PS system within the esophagus, trachea or bronchus, the amount of intervening tissue will typically be less than would be present if the PS system were positioned on the surface of the skin or even subcutaneously outside of the thoracic cavity. As may be appreciated from FIGS. 1 and 2, a portion of the esophagus E lies immediately adjacent to the heart H. Thus, as explained in more detail below, when the PS system 18 of the present invention is positioned within that portion of the esophagus E and appropriately oriented such that the emitter(s) and detectors are aimed toward the heart H, the amount of intervening tissue will be minimal. For example, if it were desired to monitor a variable within myocardial tissue, the only intervening tissue to be dealt with would be the wall of the esophagus itself. Similarly, if it is desired to monitor a variable from blood within the left ventricle LV, the only intervening tissues would the esophageal wall and the myocardium through which the NIR light passes. No skin, bone or skeletal muscle would exist between the PS system 18 and the myocardial tissue or endo-ventricular blood from which a particular variable is to be measured. Thus, in the present invention, there is no need to apply correction factors to remove spectral interference due to absorption or dispersion by any intervening skin, bone or skeletal muscle. This will provide for more accurate monitoring of the intended physiological variable within the heart or intrathoracic blood vessels. Moreover, given that the present invention avoids intervening skin, there is no need to correct for variations in skin pigment, as is the case with PS devices which are positioned on the skin surface.

In at least some embodiments of the present invention, the emitters of the PS system 18 my comprise LEDs or other suitable light emitters which emit near-infrared light having a wavelength in the range of 600-2500 nm. Ultraviolet spectroscopy would be in the range of 200-400 nm.

Figure 3:
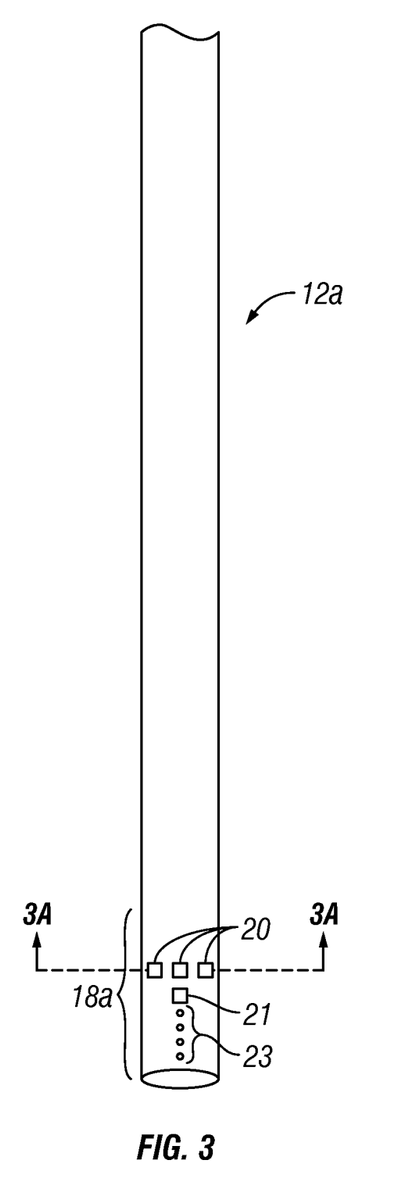
FIG. 3 shows an example of a one-piece transesophageal PS device of the present invention.
Figure 4:
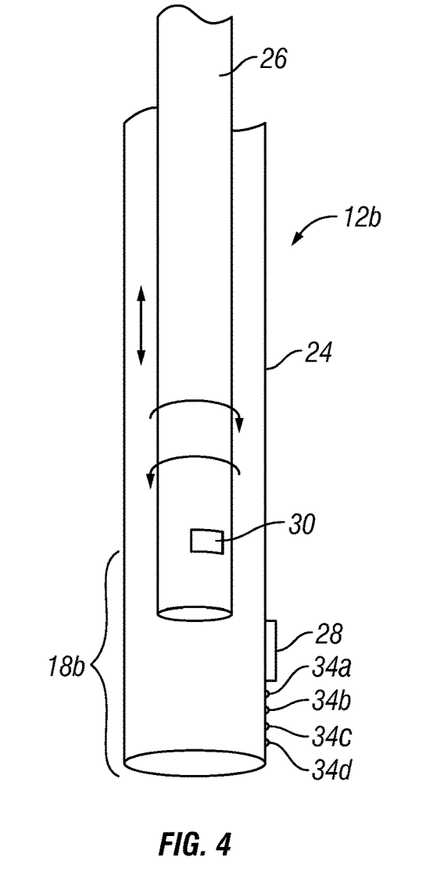
FIG. 4 shows an example of a two-piece transesophageal PS device of the present invention having a first (inner) elongate member and a second (outer) elongate member.
Figure 4A:
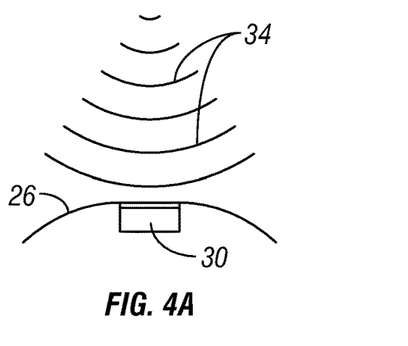
FIG. 4A is a schematic diagram showing an example of a microphone-type locator apparatus which may be incorporated in the device of FIG. 4.

In addition, in some embodiments of the invention, it may be desirable to include a locator apparatus or means for locating the specific target location from which measurements are to be obtained. Such locator apparatus may be used to facilitate maneuvering of the PS system 18 to an optimal or desirable operative location from which it will measure the desired physiological variable from the intended target location rather than some other unintended location. In some embodiments, such locator apparatus and the PS system 18 may be mounted on a single or one-piece elongate member as shown in FIG. 3. In other embodiments, it may be desirable for the locator apparatus to be positioned on one component of the elongate member 12 and the PS system 18 to be positioned on another, separately moveable component of the elongate member 12, as seen in the example of FIG. 4.

Figure 3A:
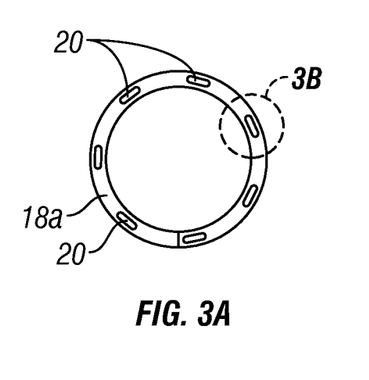
FIG. 3A is a cross-sectional view through line 3A-3A of FIG. 3.
Figure 3B:
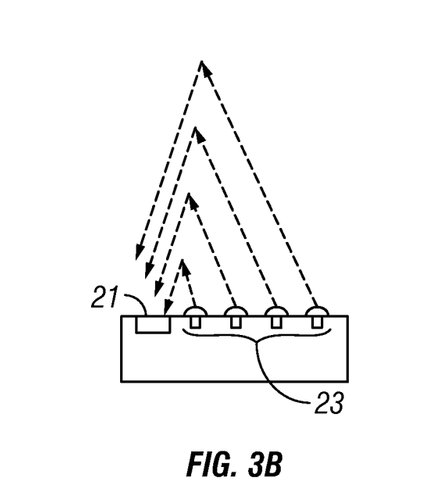
FIG. 3B is a schematic diagram showing an example of PS emitters and detector mounted on or in the transesophageal PS device of FIG. 3.

With reference to FIGS. 3-3B, there is shown an elongate member 12a that comprises a single tube having an PS system 18a near its distal end. This PS system 18a includes locator apparatus 20 as well the detector 21 and a plurality of LED light emitters 23. The locator apparatus 20 comprises a circular array of receivers, such as microphones, positioned at radially spaced-apart locations around the tube in known spatial relation to the detector 21 and emitters 23. The processor within the processing/display apparatus 14 receives signals from each of the receivers 20 in the circular array as the user longitudinally and/or rotationally moves the tube within the esophagus or other body lumen. The processor is programmed to detect when a signal received from a particular receiver 20 matches a reference signal for the intended target location. Thereafter, the user may adjust the longitudinal position and/or rotational orientation of the tube to bring the emitters and detector to the location at which the indentified receiver 20 had received a signal matching the reference signal for the intended target location. Thereafter, the PS system 18a may be used to measure the desired variable from the target location.

For example, if the receivers 20 comprise microphones and the intended target location is the heart H, the elongate member would initially be inserted into the subject's esophagus E and the processor of the processing/display apparatus 14 will poll all of the receivers (microphones) 20 in the circular array to determine which one is receiving the loudest heart beat sounds (hereinafter, the "selected receiver 20"). Thereafter, the user may move the tube longitudinally while the processor continues to poll the selected receiver 20 until the loudness of the heart sounds received by the selected receiver is peaked. At that point, the selected receiver 20 will be deemed to have located the operative position to be used. The user may then adjust the rotational orientation and/or longitudinal position of the tube within the esophagus to bring the detector 21 and emitters 23 to the operative position previously occupied by the selected receiver 20. Thereafter the intended physiological variable may be measured from the heart H by the PS system 18.

As those of skill in the art will appreciate, the simple use of heart sounds in the above example is just one example of the various types of location signatures that may be sensed by the receivers 20 and processed by the processor. Various other types of sounds or signature signals may be employed. For example, the receivers 20 and processor may be adapted to detect sound patterns or pressure wave forms of blood as it courses through specific cardiac chambers (e.g., left ventricular blood, right ventricular blood, etc.) or intrathoracic blood vessels (e.g., pulmonary artery blood, aortic blood, etc.). Alternatively, the receivers 20 and processor could be adapted to sense man-made or volitionally generated sounds, such as a series of percussive thumps applied to the chest wall at a location that is aligned with the particular intrathoracic target location from which measurements are to be obtained. Alternatively, small vibration-producing elements (e.g., vibrating devices) may be positioned on the chest wall at particular anatomical locations such as over the Apex Beat location, centrally located near to the ventricles. The vibration-producing element will performing a similar function as the man-made or volitionally generated sounds, with the added benefit that the vibration-producing element, such as a piezoelectric transducer or speaker acoustically coupled to the chest wall, can produce unique sound signatures that can be detected with higher precision than a percussive thump. For instance, in one embodiment, specific frequencies can be used for the vibration and synchronous detection may be used to more accurately detect the presence and location of the sound. Phase information determined in the synchronous detection that may be accomplished with phase-locked loops (PLLs) known to those skilled in the art may be measured from each of the sound sensors that are facing in different directions. From the amplitude and phase delay of each of the waveforms from the multiple sound sensors, it can be determined which acoustic path-length is the shortest and which may be due to reflections from the interior wall of the thoracic cavity. There may be one or more specific frequencies and phases used for the vibration. The vibration ay also be a chirp signal with steadily increasing frequency, know to those skilled in the art.

In an alternative embodiment, an inertial sensor system, such as the Analog Devices ADIS164362 Tri-Axis Gyroscope, Accelerometer may be used to map both the rotational position of the (outer) component 24 or the inner component 26 and the depth of these components 24 and 26 within the esophagus. For instance, the procedure for determining optimal depth and rotation is to take multiple sound intensity readings as the tube is slide down into the esophagus. As the tube is inserted into the esophagus and the sound sensors move closer to the heart, the amplitude of the received signals will increase, and then as the sensors pass the point where they are closest to the heart and begin to move further away from the heart, the amplitude decreases. Because the position of the tube is tracked on a continuous basis during its movement, the amplitude as a function of its position can be calculated. Once the amplitude of the sound is found to fall off by more than a threshold, e.g. 25% decrease in RMS, then the system will prompt the user to pull the tube out and rotate it until it is positioned back in the depth and rotation that generated the maximal amplitude, i.e. closest to and facing the heart.

Two inertial sensors, one positioned on the FOC and the other positioned on the SIC may be used to measure the positions of the SIC and FOC relative to each other.

Alternatively, the sensing element may include a magnetometer, such as the Analog Devices ADIS16405: High Precision Tri-Axis Gyroscope, Accelerometer, Magnetometer. Thus, instead of a sound producing element positioned on the chest wall, instead a magnetic field producing element may be positioned, such as a magnetic coil. The coil may be further configured to generate a narrow field beam such as that produced by a Helmholtz double-coil arrangement or incorporating magnetic flux concentrating elements such as ferrous materials. Alternatively, permanent magnets may also be positioned may be positioned on the chest wall at particular anatomical locations such as over the Apex Beat location, centrally located near to the ventricles, or at other locations like the supra-sternal notch. A small (0.25" diameter) Neodymium magnet (also known as NdFeB, NIB or Neo magnet), the most widely used type of rare-earth magnet, is a permanent magnet made from an alloy of neodymium, iron and boron to form the Nd2Fe14B, may be enclosed in a small self-adhesive electrode (0.5" diameter) and applied to the desired locations and used as the reference points for measuring the amplitude of the magnetic sensor output, and then used in conjunction with the inertial sensing elements of the ADIS16405 chip to map the intensity as a function of position depth and rotation.

Also, it is not necessary in all applications to use an array of separate receivers 20. In some embodiments, a single receiver 20 may be employed and the elongate member 12a may simply be moved and/or rotated until that single receiver 20 receives a signal that serves as a signature for the intended target location.

Figure 4B:
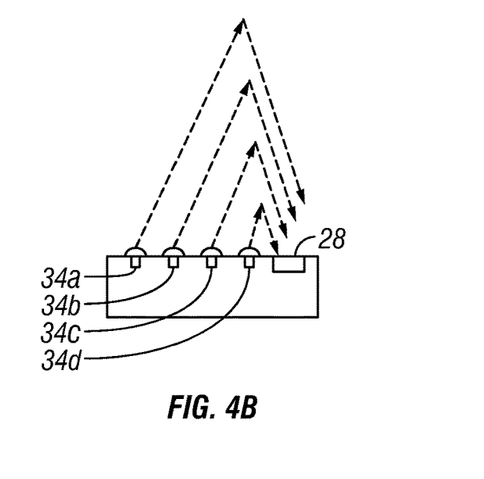
FIG. 4B is a schematic diagram showing an example of an PS system that includes a plurality of emitters and a single detector, which may be incorporated in the device of FIG. 4.
Figure 4C:
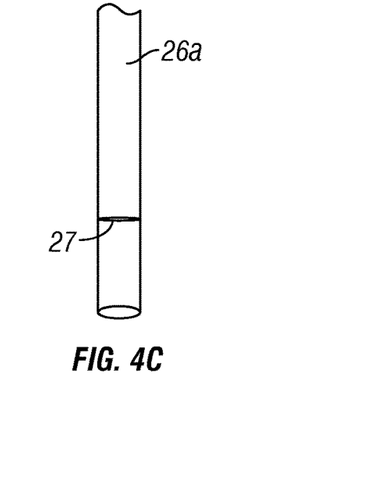
FIG. 4C shows an alternative construction for the first (inner) elongate member of the device of FIG. 4.
Figure 4D:
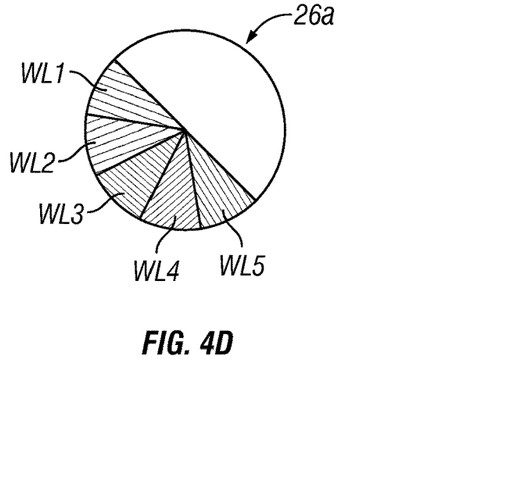
FIG. 4D is a schematic diagram illustrating a locator device having regions which sense different wavelengths of light.

FIGS. 4-4D show an example in which the elongate member 12b comprises a first (e.g., outer) component (FC) 24 which has a central cavity or through lumen and a second (e.g., inner) component (SC) 26 which is positioned within the inner cavity or lumen of the first (outer) component. The inner and outer components 24, 26 are independently advanceable/retractable and rotatable. The position of the SIC relative to the FOC, both with respect to rotation and insertion depth may in some embodiments be measured via such means as an optical encoding system or linear resistive encoder, known to those skilled in the art. In this example the locator apparatus comprises a receiver 20 (e.g., a microphone, pressure sensor or other suitable receiver) is positioned on or in the second (inner) component 26 while the PS system 18b is on or in the first (outer) component 24. As above, the PS system 18b comprises a detector 28 and plurality of emitters 34A-34d such as LEDs. The processor within the processing/display apparatus 14 receives signals from the receiver 30 as the user longitudinally and/or rotationally moves the second (inner) component 26 within the esophagus or other body lumen. The processor is programmed to detect when a signal received from the receiver 30 matches a reference signal for the intended target location. Thereafter, while the second (inner) component 26 and receiver 30 are held stationary, the user may adjust the longitudinal position and/or rotational orientation of the first (outer) component 24 as needed to bring the PS detector 28 and emitters 34a-34d into alignment with the receiver 30, thereby ensuring that the detector 28 and emitters 34a-34d are operatively positioned for acquiring the desired measurement from the intended target location rather than some other unintended location.

In some embodiments, the detector 28 may be a detector capable of measuring the incident photonic intensity at more than one wavelength or ranges of wavelengths. For instance the detector 28 may be a spectroscopic bench that is capable of generating spectrographic curves for analysis, such as is found in the Reflectance NIR system. The detector 28 may also be composed of an optical element that focuses the light incident on it onto an optically conductive pathway, e.g. a fiber optic cable that runs alongside or inside the FOC 24, and the actual sensing element of the detector is located at the distal end of the FOC. The sensing element may be a reusable element that attaches to the end of the FOC, or may in fact be located inside the processor/display 14.

In some embodiments, the receiver 30 may include an electronic, physical or other position marker to facilitate maneuvering the first (outer) component 24 to the operative position where the detector 28 and emitters 34a-34d are properly aligned with the receiver 30. For example, the receiver may emit a signal which is detected by the PS system 18b so that the PS system can be moved to a position at which it receives that signal at optimized strength, thereby indicating that the detector 28 and emitters 34a-34d are operatively aligned with the receiver 30.

In some embodiments, the processor and the PS system 18, 18a, 18b and/or locator receiver 20, 30 may employ a signal matching technique to determine when the PS system 18, 18a, 18b or receiver 20, 30 has been brought into a desired operative position relative to an intended target location. On example of this is seen in FIGS. 4C-4D. Specifically, FIG. 4C shows an alternative second (inner) component 26a for the device of FIG. 4 with a circular electrode 27. One or more second electrode(s) may be positioned on the chest wall at particular anatomical locations such as over the Apex Beat location, centrally located near to the ventricles. is used as the locator apparatus. Impedance between circular electrode 27 and such second electrode(s) is then measured as the SIC, FOC or tube is inserted into the esophagus. Optimal position is then where impedance is a minimum, using the same procedures as previously described for sound.

Using the inertial sensing system, or the optical encoding system described above, the user may be asked to rotate the SIC 24 in the two-tube system or the single tube as the device takes multiple spectroscopic measurements. Knowing the angle of the rotation via either the inertial sensor, optical encoder or other positional sensor know to those skilled in the art, a two dimensional map of the PS measurement may be created as shown in FIG. 4D, where WL1-5 are either scalar values, e.g. pH, oxygenation, fluid status, metabolic status, with an associated angular position, or can alternatively be a vector, e.g. spectroscopic measurements for instance intensity measurements at 1028 wavelengths, or alternatively the vector may include any combination of the above values and vectors for each angular measurement position. In this way, measurements can be taken of the various tissues surrounding the heart, shown in FIGS. 1 and 2. These tissues include the lungs, the great vessels and the various chambers of the heart.

Alternatively, or in addition, the system may direct the user to move the tube or SIC up or down the esophagus for two or more measurement cycles to create a two dimensional map of measurements along the length of the tube, in much the same way is it does for rotationally-oriented measurements. Additionally the measurement sets may be combined to create a three-dimensional measurement, with multiple "slices" of axial measurement sets. Alternatively, the position of the SIC 26 relative to the FOC 24 may be accomplished via actuators controlled by the device. The actuators may take the form of a cylindrical motor positioned on the distal end of the FOC that is able to roll the SIC 26 up and down relative to the FOC 24 and also rotate the SIC 26 relative to the FOC 24.

Because there are multiple emitters 34 spaced from the detector 28, measurements can be taken for varying depths into the tissue as shown in FIG. 4B. Thus, in addition to the three-dimensional measurement map as shown in FIG. 4D, measurements can be made specifically of the individual tissues within the vicinity of the esophagus. For instance, emitter 34d will generate measurements primarily of the esophageal tissue itself, while emitter 34b and 34c will generate measurements of the lungs on the right side (WL2 and WL3) and the myocardium on the left side (WL5), while emitter 34a extends to the greatest depth and will generate measurements predominantly of the blood itself within the chambers of the heart (WL5). Additionally, the spectra generated from the emitters 34 closer to the detector 28 may be spectrally subtracted from the spectra of the emitters farther away (e.g. 34a) in order to accentuate the spectral content due to the tissue further away from the sensor/emitters.

Alternatively, multiple reference sound, magnetic or impedance sources may be positioned circumferentially at roughly the angular position of the WLs in FIG. 4D. The multiple sources may be built into a circumferential band that is applied around the patient's thorax or be self-adhesively-applied to the front of the patient's chest.

Figure 5A:
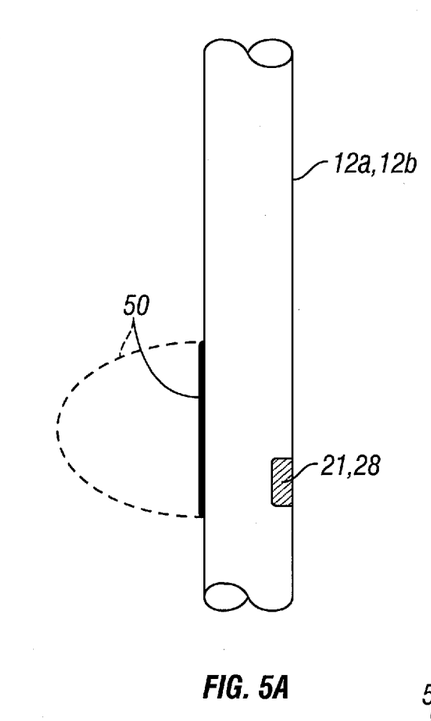
FIG. 5A is a schematic diagram showing a device of the present invention having one type of apparatus for compressing at least the PS detector against the wall of the esophagus at a desired location.
Figure 5B:
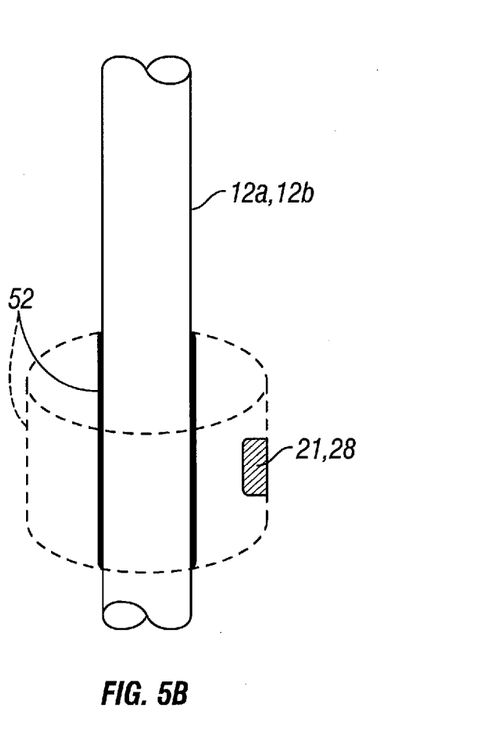
FIG. 5B is a schematic diagram showing a device of the present invention having another type of apparatus for compressing at least the PS detector against the wall of the esophagus at a desired location.

In at least some embodiments of the invention, it will be desirable for the PS system 18 or portion(s) thereof to be placed in direct contact with the wall of the body lumen (e.g., esophagus, trachea or bronchus) in which it is positioned while obtaining the desired measurements. Thus, any of the devices of the present inventions may optionally be equipped with balloons, expandable members, projectable members or other apparatus for placing the PS system 18 or any relevant portion(s) thereof (e.g., the detector and/or emitter(s)) in close or abutting contact with the wall of the body lumen in which it is positioned. FIGS. 5A and 5B show non-limiting examples of balloons that may be used for this purpose.

In FIG. 5A, a balloon 50 is positioned on one side of the elongate member 12 diametrically opposite the detector 21, 28 of the PS system 18. In this manner, once the PS system has been maneuvered to the operative position, the balloon 50 may be inflated so that it contacts the wall on one side of the body lumen opposite the operative location and forces the detector 21, 28 (and/or other portions of the PS system) into contact with the wall of the body lumen at the operative location.

In FIG. 5B, a generally annular or torioidal balloon cuff 52 is mounted on the elongate member 12 and the detector 21, 28 and/or other portions of the PS system 18 is mounted at a particular radial location on the wall of the balloon cuff 52. After the elongate member has been maneuvered to place the detector 21, 28 (and/or other portions of the PS system) at the appropriate longitudinal and rotational position, the balloon cuff 52 is then inflated until it coapts with the surrounding wall of the body lumen, thereby placing the detector 21, 28 (and/or other portions of the PS system) in contact with the wall of the body lumen at the operative location.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the substantial absence of other elements, steps, members, components, compositions, reactants, parts or portions unless otherwise noted. All reasonable additions, deletions, modifications and alterations are to be considered equivalents of the described examples and embodiments and are to be included within the scope of the following claims.

What is claimed is:

1. A system useable for monitoring a physiological variable in a target tissue or body fluid located within the thorax of a subject by optical spectroscopy, said system comprising:
   an elongate body configured for insertion into the esophagus, trachea or bronchus of the subject;
   an optical spectroscopy system which is useable for measuring the physiological variable located on or in the elongate body, said optical spectroscopy system comprising i) an emitter for emitting light in the wavelength range of 200-2500 nm through the wall of the esophagus and into a target tissue or body fluid located in the heart, chamber of the heart or intrathoracic blood vessel and ii) a detector for detecting light that has been emitted from the emitter after said light has undergone dispersion and/or reflection by the target tissue or body fluid;
   a positional sensor system useable to track rotational and longitudinal movement of the elongate member within the trachea, esophagus or bronchus relative to the location of the target tissue or body fluid; and
   a processing device which receives signals from the positional sensor system and optical spectroscopy system, said processing device being programmed to a) use signals received from the positional sensor system to determine an optimal position of the elongate member for monitoring the target tissue or body fluid by the optical spectroscopy system and b) use signals received from the optical spectroscopy system, while the elongate member is positioned at the optimal position, to estimate at least one physiological variable within the target tissue or body fluid.

2. A system according to claim 1 wherein said at least one physiological variable comprises a variable selected from the group consisting of: temperature, oxygen tension, oxygen saturation, partial pressure of oxygen, partial pressure of carbon dioxide, hemoglobin concentration, water concentration, hematocrit, glucose concentration and presence of a biomarker.

3. system according to claim 1 wherein the processing device a) receives spectral information from the detector, b) compares that spectral information to a set of spectra determined from a model for light attenuation in the sample to identify a member of the set of spectra that corresponds to the measured spectral information; c) corrects the identified member of the set of spectra using a set of spectral correction factors determined from the set of spectra; and d) uses the corrected identified member of the set of spectra as input to a calibration equation to determine a value associated with the particular physiological variable being measured.

4. A system according to claim 1 wherein the emitter is configured to emit near-infrared light having a wavelength in the range of 600-660 nm.

5. A system according to claim 1 wherein the emitter is configured to emit near-infrared light having a wavelength in the range of 200-400 nm.

6. A system according to claim 1 wherein the emitter is configured to emit near-infrared light having a wavelength in the range of 400-600 nm.

7. A system according to claim 1 wherein the emitter is configured to emit near-infrared light having a wavelength in the range of 600-2500 nm.

8. A system according to claim 1 wherein the emitter comprises at least one light emitting diode.

9. A system according to claim 1 further comprising a locator apparatus on a the elongate body, said locator apparatus being useable to locate a desired position for the emitter and detector relative to the target tissue or body fluid, wherein the elongate body is longitudinally and rotationally moveable within the esophagus or trachea to cause the emitter and detector to be positioned at said desired location.

10. A system according to claim 9 wherein the locator apparatus is selected from: microphones, stethoscopes, other sound detectors, electrical impulse detectors, electrocardiographic signal detectors, pressure sensors, pressure wave form sensors and detectors which detect user-generated location signals.

11. A system according to claim 9 wherein the locator apparatus is mounted on or in the elongate body in fixed spatial relation to at least the detector such that, when the locator apparatus has become aligned with a predetermined target, at least the detector will be positioned to receive light that has been emitted from the emitter after said light has undergone dispersion and/or reflection by the target tissue or body fluid.

12. A system according to claim 9 wherein the elongate body comprises a first elongate member which has the emitter and detector mounted thereon or therein and a second elongate member which has the locator apparatus mounted thereon or therein, wherein the second elongate member is moveable within the esophagus or trachea until the locator apparatus has located the desired position for the emitter and detector and, thereafter, the first elongate member is moveable to an operative position relative to the locator apparatus, said operative position causing the emitter and detector to be positioned at said desired location.

13. A system according to claim 12 wherein the first elongate member comprises a tube having a lumen and the second elongate member is insertable into and moveable within the lumen of the first elongate member.

14. A system according to claim 12 wherein the locator apparatus further comprises a position marker which is useable to facilitate maneuvering the second elongate apparatus to a position where the infrared spectroscopy system is operatively aligned with the then-current position of the locator apparatus.

15. A system according to claim 14 wherein the position marker comprises a signal emitter on either the locator apparatus or the second elongate apparatus and a signal receiver on the other, the signal receiver being operative to receive a signal from the signal emitter.

16. A system according to claim 15 wherein the signal receiver provides an indication of when the near infrared spectroscopy system is operatively aligned with the then-current position of the locator apparatus.

17. A system according to claim 12 wherein the detector comprises a sensing element located at a distal end of the first elongate member.

18. A system according to claim 12 wherein said at positional sensor system is useable for determining a rotational, transverse or longitudinal position of the first elongate member relative to the position of the second elongate member.

19. A system according to claim 18 wherein said positional sensor system determines the rotational orientation of the first elongate member relative to the rotational orientation of the second elongate member.

20. A system according to claim 18 wherein said positional sensor system determines the insertion depth of the first elongate member relative to the insertion depth of the second elongate member.

21. A system according to claim 18 wherein said positional sensor system comprises optical encoding system.

22. A system according to 18 said positional sensor system comprises a linear resistive encoder.

23. A system according to claim 18 wherein said positional sensor system comprises an inertial sensor system.

24. A system according to claim 18 wherein said positional sensor system comprises a magnetometer device.

25. A system according to claim 9 wherein the processing device compares signals sensed by the locator apparatus to one or more reference signals, each reference signal being associated with a different tissue or body fluid within the subject's thorax.

26. A system according to claim 25 wherein said reference signals are associated with one or more tissues or body fluids selected from; myocardial tissue, blood within the left ventricle, blood within the right ventricle, blood within the right atrium, blood within the pulmonary artery, blood within a pulmonary vein and blood within the aorta.

27. A system according to claim 25 further comprising a user interface whereby a user may select a target reference signal from a plurality of stored reference signals and wherein the processing device is programmed to then compares signals received from the locator apparatus to the selected target reference signal.

28. A system according to claim 27 further comprising a notification apparatus which issues a notification to the user when the signal received the locator apparatus matches the selected target signal, thereby indicating that the locator apparatus is currently in an operative position relative to the target tissue or body fluid.

29. A system according to claim 9 wherein the locator apparatus has a plurality of zones, each of said zones being programmed to compare signal received from the locator apparatus with a different reference signal, wherein each reference signal is associated with a different tissue or body fluid within the thorax of the subject.

30. A system according to claim 29 further comprising a user interface by which a user may select a particular zone that is programmed with a reference signal that is associated with a target tissue or body fluid to be monitored.

31. A system according to claim 30 further comprising a notification apparatus which issues a notification to the user when the the selected zone is receiving a sensed signal that matches the target signal for which that zone is programmed so as to indicate that the locator apparatus is operatively positioned relative to the desired target location.

32. A system according to claim 1 wherein the detector measures incident photonic intensity at more than one wavelength or more than one wavelength range.

33. A system according to claim 32 wherein the detector comprises a spectroscopic bench capable of generating spectrographic curves for analysis.

34. A system according to claim 1 wherein the detector comprises an optical element that focuses incident light into an optically conductive pathway that runs along the elongate body to the processing device or other apparatus.

35. A system according to claim 1 wherein the detector comprises a reuseable sensing element that is attachable to and detachable from the elongate body.

36. A system according to claim 1 further comprising a signaling device positionable on the exterior surface of the subject's chest at a location having a known spatial relationship to an intrathoracic location from which it is desired to measure the physiological variable and wherein the detector or other apparatus on the elongate body is adapted to sense a signal from the signaling device thereby providing information whereby a user may maneuver the elongate body to a position and rotational orientation suitable for measuring the physiological variable from the intended intrathoracic location.

37. A system a ding to claim 36 wherein the signaling device comprises a vibrating device, piezoelectric transducer, percussive device, acoustical device, speaker, magnetic field producing device, an electromagnetic coil, an electromagnetic coil adapted to generate a narrow field beam, a Helmholtz double-coil or an electromagnetic coil which incorporates a ferrous metal or other magnetic flux concentrating element.

38. A system according to claim 36 wherein the signaling device is positionable on the subject's chest directly above the Apex Beat Location.

39. A system according to claim 1 wherein the positional sensor system includes at least one movement sensor that emits signals indicating changes in the rotational and longitudinal position of the elongate member and at least one sound sensor which emits signals indicating proximity to sounds emanating from the target tissue or body fluid.

40. A system according to claim 39 wherein said at least one sound sensor emits signals of increasing amplitude as the elongate member approaches said optimal position and decrease in amplitude as the as the elongate member diverge from said optimal position.

41. A system according to claim 40 wherein the processing device is programmed to calculate the amplitude of signals received from said at least one sound sensor as a function of the rotational and longitudinal position of the elongate member as indicated by signals from said at least one movement sensor.

42. A system according to claim 39 wherein said at least one movement sensor comprises a sensor selected from: inertial sensors, gyroscopes, accelerometers, optical encoders and magnetometers.

* * * * *